United States Patent [19]

Ozaki et al.

[11] Patent Number: 5,482,951
[45] Date of Patent: Jan. 9, 1996

[54] TRIAZOLE DERIVATIVES AS WELL AS INSECTICIDE AND ACARICIDE

[75] Inventors: Masami Ozaki; Atsuhiko Ikeda; Reijiro Honami; Takashi Yumita; Naokazu Minoguchi; Hiroyuki Yano; Norihiko Izawa; Tadayoshi Hirano, all of Shizuoka, Japan

[73] Assignees: Kumiai Chemical Industry Co., Ltd.; Ihara Chemical Industry Co., Ltd., both of Tokyo, Japan

[21] Appl. No.: 172,191

[22] Filed: Dec. 23, 1993

Related U.S. Application Data

[63] Continuation-in-part of Ser. No. 956,984, Oct. 6, 1992, Pat. No. 5,318,959.

[30] Foreign Application Priority Data

May 29, 1992 [JP] Japan ..................... 4-161759

[51] Int. Cl.$^6$ .................. A61K 31/41; A61K 31/44; C07D 213/16; C07D 249/08
[52] U.S. Cl. .................. 514/340; 514/383; 546/276; 548/266.2
[58] Field of Search .................. 548/266.2; 514/383, 514/340; 546/276

[56] References Cited

U.S. PATENT DOCUMENTS

| | | | |
|---|---|---|---|
| 4,011,218 | 3/1977 | Baldwin et al. | 260/250 |
| 4,414,221 | 11/1983 | Parsons et al. | 514/383 |
| 4,788,210 | 11/1988 | Lüthy et al. | 514/383 |
| 5,196,537 | 3/1993 | Reitz | 546/276 |

FOREIGN PATENT DOCUMENTS

| | | |
|---|---|---|
| 0036711 | 9/1981 | European Pat. Off. . |
| 0185256 | 6/1988 | European Pat. Off. . |
| 3631511 | 9/1986 | Germany . |

OTHER PUBLICATIONS

Synthesis, (Jun. 1983), pp. 483–486, Perez et al, "Regioselective Synthesis of 1,2,4-Triazole and 1,2,4-Oxidiazole Deri . . . ".

Bulletin of the Chemical Society of Japan, vol. 56, pp. 545–548 (1983) Ito et al, "N–Methyl–N–(phenylSulfonyl)benzohydrazonoyl Chl . . . ".

Research Disclosure RD278004 (with Abstract), "New 3,5-Di:aryl-1-Methyl-1,2,4-Triazole Derivs. & Useful as Acaricides and . . . " (1967).

*Primary Examiner*—Robert W. Ramsuer
*Assistant Examiner*—Laura R. Cross
*Attorney, Agent, or Firm*—Stevens, Davis, Miller & Mosher

[57] ABSTRACT

A novel triazole derivative for use in an insecticide or an acaricide has a general formula [I]:

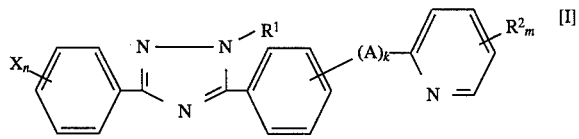

(wherein $R^1$ is an alkyl group, X is a hydrogen atom, a halogen atom or the like, n is an integer of 1–5, A is an oxygen atom, a sulfur atom or the like, k is 0 or 1, $R^2$ is a hydrogen atom, a halogen atom or the like, m is an integer of 1–5) and controls various injurious insects and mites, particularly mites and aphids without damaging crops.

9 Claims, No Drawings

TRIAZOLE DERIVATIVES AS WELL AS INSECTICIDE AND ACARICIDE

This application is a continuation-in-part of the application Ser. No. 07/956,984 filed Oct. 6, 1992, now U.S. Pat. No. 5,318,959.

BACKGROUND OF THE INVENTION

1. Field of the Invention

This invention relates to novel triazole derivative as well as insecticide and acaricide containing the same as an active ingredient.

2. Description of the Related Art

Japanese Patent laid open No. 56-154464 and DE-A-3631511 disclose that various triazole derivatives develop insecticidal and acaricidal activities. However, it can not be said that the insecticidal and acaricidal activities of these compounds described in these specifications are satisfactory.

Up to the present, various compounds such as organophosphorus compound, organotin compound and the like have been used for the control of pests in farm and garden crops and mites. However, these compounds have been used over many years, so that the above injurious insects have a resistance to chemicals to a certain extent and it recently becomes difficult to control these insects. Particularly, this tendency is conspicuous in lepidopteran injurious insects, mites and aphids and becomes serious. As a result, it is demanded to develop new types of insecticide and acaricide having a different function.

SUMMARY OF THE INVENTION

The inventors have made various studies in order to create novel insecticides and acaricides having a very high effect against wide injurious pests and capable of safely using, which have never been found in the conventional technique, in the development of the insecticide and acaricide having a function different from that of the conventional one.

Further, the inventors have synthesized various triazole derivatives and examined their physiological activities. As a result, the inventors have found that novel triazole derivatives having a general formula [I] as mentioned later have an excellent effect against wide injurious pests in farm and garden crops, particularly lepidopteran injurious insects, mites and aphids and also develop a very high effect against eggs and larvae of mites and larvae of aphids having a resistance to the conventional chemicals, and the invention has been accomplished.

According to the invention, there is the provision of a triazole derivative having the following general formula [I]:

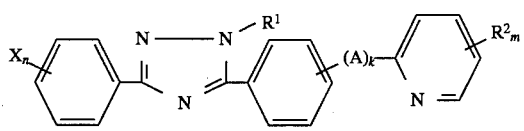

(wherein $R^1$ is an alkyl group, X is a hydrogen atom, a halogen atom, an aklyl group, an alkoxy group, an alkylthio group, a nitro group, a cyano group or trifluoromethyl group, n is an integer of 1–5 provided that when n is 2 or more, X may be an optional combination of same or different atoms or groups, A is an oxygen atom, a sulfur atom, a lower alkylene group, a lower alkyleneoxy group, an oxy-lower alkylene group or a lower alkyleneoxyalkylene group, k is 0 or 1, $R^2$ is a hydrogen atom, a halogen atom, an alkyl group, an alkoxy group, trifluoromethyl group or trifluoromethoxy group, and m is an integer of 1–5 provided that when m is 2 or more, $R^2$ may be an optional combination of same or different atoms or groups).

Furthermore, the invention provides an insecticide or an acaricide containing the above triazole derivative as an active ingredient.

Throughout the specification, the term "lower" means that the carbon number in the group added with this term is not more than 6.

Further, the term "alkyl group" means a straight or branched-chain alkyl group having a carbon number of 1–30, which includes, for example, methyl group, ethyl group, n-propyl group, isopropyl group, n-butyl group, isobutyl group, sec-butyl group, t-butyl group, n-pentyl group, isoamyl group, neopentyl group, n-hexyl group, isohexyl group, 3,3-dimethylbutyl group, n-heptyl group, 5-methylhexyl group, 4-methylhexyl group, 3-methylhexyl group, 4,4-dimethylpentyl group, n-octyl group, 6-methylheptyl group, n-nonyl group, 7-methyloctyl group, n-decyl group, 8-methylnonyl group, n-undecyl group, 9-methyldecyl group, n-dodecyl group, 10-methylundecyl group, n-tridecyl group, 11-methyldodecyl group, n-tetradecyl group, 12-methyltridecyl group, n-pentadecyl group, 13-methyl-tetradecyl group, n-hexadecyl group, n-heptadecyl group, n-octadecyl group, n-nonadecyl group, n-eicosyl group and the like.

The terms "alkoxy group" and "alkylthio group" are (alkyl)-O— group and (alkyl)-S— group in which the alkyl portion has the same meaning as mentioned above, respectively.

The term "halogen atom" means fluorine, chlorine, bromine and iodine.

The term "lower alkylene group" means a straight or branched-chain alkylene group having a carbon number of 1–4, which includes, for example, —$CH_2$—, —$CH_2CH_2$—, —$CH(CH_3)$—, —$CH_2CH_2CH_2$—, —$CH(CH_3)CH_2$—, —$C(CH_3)_2$—, —$CH_2CH_2CH_2CH_2$—, —$CH(CH_3)CH_2CH_2$—, —$CH_2CH(CH_3)CH_2$— and the like.

The term "lower alkyleneoxy group" means -(lower alkylene)-O— group in which the lower alkylene portion has the same meaning as mentioned above.

The term "oxy-lower alkylene group" means —O-(lower alkylene)- group in which the lower alkylene portion has the same meaning as mentioned above.

The term "lower alkyleneoxyalkylene group" means -(lower alkylene)-O-(lower alkylene)- group in which the lower alkylene portion has the same meaning as mentioned above.

DESCRIPTION OF THE PREFERRED EMBODIMENTS

As a preferable compound according to the invention, there are mentioned compounds having the general formula [I] wherein $R^1$ is a straight or branched-chain alkyl group having a carbon number of 1–6, preferably methyl group, X is a hydrogen atom, a halogen atom, a straight or branched-chain alkyl group having a carbon number of 1–4, a nitro group, a cyano group or trifluoromethyl group, n is an integer of 1–3 provided that when n is 2 or 3, X may be an optional combination of same or different atoms or groups, A is an oxygen atom, a sulfur atom, a lower alkylene group having a carbon number of 1–4, methyleneoxy group or oxymethylene group, k is 0 or 1, $R^2$ is a hydrogen atom, a halogen atom, a lower alkyl group, a lower alkoxy group, trifluoromethyl group or trifluoromethoxy group, and m is an integer of 1–3 provided that when m is 2 or 3, $R^2$ may be an optional combination of same or different atoms or groups).

Concrete examples of the compounds having the general formula [I] according to the invention are shown in Table 1 to 8. Moreover, the compound No. is referred in subsequent description.

TABLE 1

$$X_n\text{-}\underset{}{\phenyl}\text{-}\underset{N}{\overset{N-N(R^1)}{C}}\text{-}\phenyl\text{-}(A)_k\text{-}\underset{N}{\pyridyl}\text{-}R^2_m$$

| Compound No. | $R^1$ | $X_n$ | Substitution position | $(A)_k$ | $R^2_m$ | Melting point (°C.) or refractive index ($n_D^{20}$) |
|---|---|---|---|---|---|---|
| 1 | $CH_3$ | 2-Cl | 4- | O | H | |
| 2 | $CH_3$ | 2-Cl,6-F | 4- | O | H | 122.0–127.0 |
| 3 | $CH_3$ | 2-Cl | 4- | O | 5-$CF_3$ | 107.0–109.0 |
| 4 | $CH_3$ | 2-Cl,6-F | 4- | O | 5-$CF_3$ | 94.0–96.0 |
| 5 | $CH_3$ | 2-Cl | 4- | O | 3-Cl,5-$CF_3$ | not measurable |
| 6 | $CH_3$ | 2-Cl,6-F | 4- | O | 3-Cl,5-$CF_3$ | not measurable |
| 7 | $CH_3$ | 2-Cl | 4- | S | 3-Cl,5-$CF_3$ | 127.0–131.0 |
| 8 | $CH_3$ | 2-Cl | 4- | $CH_2O$ | H | |
| 9 | $CH_3$ | 2-Cl,6-F | 4- | $CH_2O$ | H | |
| 10 | $CH_3$ | 2-Cl,6-F | 2- | O | 5-$CF_3$ | 126.0–129.0 |
| 11 | $CH_3$ | 2-Cl,6-F | 3- | O | H | not measurable |
| 12 | $CH_3$ | 2-Cl,6-F | 3- | O | 5-Cl | not measurable |
| 13 | $CH_3$ | 2,6-$F_2$ | 3- | O | 5-Cl | |
| 14 | $CH_3$ | 2-Cl,6-F | 3- | O | 6-Cl | 124.0–127.0 |
| 15 | $CH_3$ | 2,6-$F_2$ | 3- | O | 6-Cl | |
| 16 | $CH_3$ | 2-Cl,6-F | 3- | O | 4-$CH_3$ | |
| 17 | $CH_3$ | 2-Cl,6-F | 3- | O | 5-$CH_3$ | not measurable |
| 18 | $CH_3$ | 2-Cl,6-F | 3- | O | 6-$CH_3$ | not measurable |
| 19 | $CH_3$ | 2-Cl,6-F | 3- | O | 4-$C_2H_5$ | |
| 20 | $CH_3$ | 2-Cl,6-F | 3- | O | 6-$C_3H_7$ | |
| 21 | $CH_3$ | 2-Cl | 3- | O | 3-$CF_3$ | not measurable |
| 22 | $CH_3$ | 2-Cl,6-F | 3- | O | 3-$CF_3$ | 122.0–124.0 |
| 23 | $CH_3$ | 2,6-$F_2$ | 3- | O | 3-$CF_3$ | |
| 24 | $CH_3$ | 2-Cl,6-F | 3- | O | 4-$CF_3$ | 1.5820 |

TABLE 2

| Compound No. | $R^1$ | $X_n$ | Substitution position | $(A)_k$ | $R^2m$ | Melting point (°C.) or refractive index ($n_D^{20}$) |
|---|---|---|---|---|---|---|
| 25 | $CH_3$ | 2,6-$F_2$ | 3- | O | 4-$CF_3$ | |
| 26 | $CH_3$ | 2-Cl,6-F | 3- | O | 5-$CF_3$ | |
| 27 | $CH_3$ | 2-Cl | 3- | O | 5-$CF_3$ | not measurable |
| 28 | $CH_3$ | 2-Cl,6-F | 3- | O | 5-$CF_3$ | 65.0–68.0 |
| 29 | $CH_3$ | 2,6-$F_2$ | 3- | O | 5-$CF_3$ | not measurable |
| 30 | $CH_3$ | 2,6-$Cl_2$ | 3- | O | 5-$CF_3$ | |
| 31 | $CH_3$ | 2-Cl,6-F | 3- | S | 5-$CF_3$ | 82.0–86.0 |
| 32 | $CH_3$ | 2-Cl,6-F | 3- | $CH_2$ | 5-$CF_3$ | |
| 33 | $CH_3$ | 2-Cl | 3- | $CH_2O$ | 5-$CF_3$ | |
| 34 | $CH_3$ | 2-Cl,6-F | 3- | $CH_2O$ | 5-$CF_3$ | 96.0–97.5 |
| 35 | $CH_3$ | 2,6-$F_2$ | 3- | $CH_2O$ | 5-$CF_3$ | |
| 36 | $CH_3$ | 2,6-$Cl_2$ | 3- | $CH_2O$ | 5-$CF_3$ | |
| 37 | $CH_3$ | 2-Cl,6-F | 3- | $C_2H_4O$ | 5-$CF_3$ | |
| 38 | $CH_3$ | 2-Cl,6-F | 3- | O | 6-$CF_3$ | 98.0–102.0 |
| 39 | $CH_3$ | 2,6-$F_2$ | 3- | O | 6-$CF_3$ | |
| 40 | $CH_3$ | 2-Cl,6-F | 3- | O | 5-Cl,3-$CF_3$ | |
| 41 | $CH_3$ | 2,6-$F_2$ | 3- | O | 5-Cl,3-$CF_3$ | |
| 42 | $CH_3$ | 2-Cl | 3- | O | 5-Cl,3-$CF_3$ | 71.0–73.0 |

TABLE 2-continued

| Compound No. | $R^1$ | $X_n$ | Substitution position | $(A)_k$ | $R^2m$ | Melting point (°C.) or refractive index ($n_D^{20}$) |
|---|---|---|---|---|---|---|
| 43 | $CH_3$ | 2-Cl,6-F | 3- | O | 5-Cl,3-$CF_3$ | 109.0–111.0 |
| 44 | $CH_3$ | 2,6-$F_2$ | 3- | O | 5-Cl,3-$CF_3$ | |
| 45 | $CH_3$ | 2-Cl | 3- | O | 3-Cl,5-$CF_3$ | not measurable |
| 46 | $CH_3$ | 2-Cl,6-F | 3- | O | 3-Cl,5-$CF_3$ | not measurable |
| 47 | $CH_3$ | 2,6-$F_2$ | 3- | O | 3-Cl,5-$CF_3$ | 115.0–116.0 |
| 48 | $CH_3$ | 2-Cl,6-F | 3- | O | 3,5-$(CF_3)_2$ | 91.0–95.0 |
| 49 | $CH_3$ | 2,6-$F_2$ | 3- | O | 3,5-$(CF_3)_2$ | |
| 50 | $CH_3$ | 2-Cl,6-F | 3- | O | 6-Cl,5-$CF_3$ | not measurable |
| 51 | $CH_3$ | 2,6-$F_2$ | 3- | O | 6-Cl,5-$CF_3$ | |
| 52 | $CH_3$ | 2-Cl,6-F | 3- | O | 4,5-$(CF_3)_2$ | 122.0–126.0 |
| 53 | $CH_3$ | 2,6-$F_2$ | 3- | O | 4,5-$(CF_3)_2$ | |

TABLE 3

| Compound No. | $R^1$ | $X_n$ | Substitution position | $(A)_k$ | $R^2m$ | Melting point (°C.) or refractive index ($n_D^{20}$) |
|---|---|---|---|---|---|---|
| 54 | $CH_3$ | 2-Cl,6-F | 3- | O | 6-Cl,4-$CF_3$ | not measurable |
| 55 | $CH_3$ | 2,6-$F_2$ | 3- | O | 6-Cl,4-$CF_3$ | |
| 56 | $CH_3$ | 2-Cl,6-F | 3- | O | 4,6-$(CF_3)_2$ | 1.5453 |
| 57 | $CH_3$ | 2,6-$F_2$ | 3- | O | 4,6-$(CF_3)_2$ | |
| 58 | $CH_3$ | 2-Cl,6-F | 3- | O | 6-$CH_3$,4-$CF_3$ | 121.0–123.0 |
| 59 | $CH_3$ | 2,6-$F_2$ | 3- | O | 6-$CH_3$,4-$CF_3$ | |
| 60 | $CH_3$ | 2-Cl,6-F | 4- | O | 5-Cl | 136.0–139.0 |
| 61 | $CH_3$ | 2,6-$F_2$ | 4- | O | 5-Cl | |
| 62 | $CH_3$ | 2-Cl,6-F | 4- | O | 6-Cl | 134.0–136.0 |
| 63 | $CH_3$ | 2,6-$F_2$ | 4- | O | 6-Cl | |
| 64 | $CH_3$ | 2-Cl,6-F | 4- | O | 4-$CH_3$ | 136.0–140.0 |
| 65 | $CH_3$ | 2-Cl,6-F | 4- | O | 4-$C_2H_5$ | |
| 66 | $CH_3$ | 2-Cl,6-F | 4- | O | 5-$CH_3$ | 154.0–157.0 |
| 67 | $CH_3$ | 2-Cl,6-F | 4- | O | 6-$CH_3$ | not measurable |
| 68 | $CH_3$ | 2-Cl,6-F | 4- | O | 6-$C_3H_7$ | |
| 69 | $CH_3$ | 2-Cl,6-F | 4- | O | 3-$CF_3$ | 158.0–159.9 |
| 70 | $CH_3$ | 2,6-$F_2$ | 4- | O | 3-$CF_3$ | |
| 71 | $CH_3$ | 2-Cl,6-F | 4- | O | 4-$CF_3$ | 110.0–114.0 |
| 72 | $CH_3$ | 2,6-$F_2$ | 4- | O | 4-$CF_3$ | |
| 73 | $CH_3$ | 2-Cl,6-F | 4- | — | 5-$CF_3$ | |
| 74 | $CH_3$ | 2,6-$F_2$ | 4- | — | 5-$CF_3$ | |
| 75 | $C_2H_5$ | 2-Cl,6-F | 4- | O | 5-$CF_3$ | not measurable |
| 76 | $CH(CH_3)_2$ | 2-Cl,6-F | 4- | O | 5-$CF_3$ | not measurable |
| 77 | $CH_3$ | 2,6-$F_2$ | 4- | O | 5-$CF_3$ | 127.0–131.0 |
| 78 | $CH_3$ | 2,6-$Cl_2$ | 4- | O | 5-$CF_3$ | 127.0–130.0 |
| 79 | $C_6H_{13}$ | 2-Cl,6-F | 4- | O | 5-$CF_3$ | 1.5573 |
| 80 | $CH_3$ | 2-Cl | 4- | S | 5-$CF_3$ | not measurable |
| 81 | $CH_3$ | 2-Cl,6-F | 4- | S | 5-$CF_3$ | 111.0–115.0 |
| 82 | $CH_3$ | 2,6-$F_2$ | 4- | S | 5-$CF_3$ | |

TABLE 4

| Compound No. | $R^1$ | $X_n$ | Substitution position | $(A)_k$ | $R^2m$ | Melting point (°C.) or refractive index ($n_D^{20}$) |
|---|---|---|---|---|---|---|
| 83 | $CH_3$ | 2,6-$Cl_2$ | 4- | S | 5-$CF_3$ | |
| 84 | $CH_3$ | 2-Cl,6-F | 4- | $CH_2$ | 5-$CF_3$ | |
| 85 | $CH_3$ | 2,6-$F_2$ | 4- | $CH_2$ | 5-$CF_3$ | |
| 86 | $CH_3$ | 2-Cl | 4- | $CH_2O$ | 5-$CF_3$ | |
| 87 | $CH_3$ | 2-Cl,6-F | 4- | $CH_2O$ | 5-$CF_3$ | 1.5859 |
| 88 | $CH_3$ | 2,6-$F_2$ | 4- | $CH_2O$ | 5-$CF_3$ | |
| 89 | $CH_3$ | 2,6-$Cl_2$ | 4- | $CH_2O$ | 5-$CF_3$ | |
| 90 | $CH_3$ | 2-Cl,6-F | 4- | $C_2H_4O$ | 5-$CF_3$ | |

TABLE 4-continued

| Compound No. | $R^1$ | $X_n$ | Substitution position | $(A)_k$ | $R^2m$ | Melting point (°C.) or refractive index ($n_D^{20}$) |
|---|---|---|---|---|---|---|
| 91 | $CH_3$ | 2-Cl,6-F | 4- | O | 6-$CF_3$ | 97.0–101.0 |
| 92 | $CH_3$ | 2-Cl,6-F | 4- | O | 3,5-$Cl_2$ | 53.0–57.0 |
| 93 | $CH_3$ | 2-Cl,6-F | 4- | O | 5-Cl,3-$CF_3$ | not measurable |
| 94 | $CH_3$ | 2,6-$F_2$ | 4- | O | 5-Cl,3-$CF_3$ | |
| 95 | $CH_3$ | 2-Cl,6-F | 4- | S | 3-Cl,5-$CF_3$ | not measurable |
| 96 | $CH_3$ | 2,6-$F_2$ | 4- | S | 3-Cl,5-$CF_3$ | |
| 97 | $CH_3$ | 2-Cl,6-F | 4- | $CH_2O$ | 3-Cl,5-$CF_3$ | 73.0–75.0 |
| 98 | $CH_3$ | 2,6-$F_2$ | 4- | $CH_2O$ | 3-Cl,5-$CF_3$ | 132.0–136.0 |
| 99 | $CH_3$ | 2-Cl,6-F | 4- | O | 3,5-$(CF_3)_2$ | 85.0–89.0 |
| 100 | $CH_3$ | 2,6-$F_2$ | 4- | O | 3,5-$(CF_3)_2$ | |
| 101 | $CH_3$ | 2-Cl,6-F | 4- | O | 6-Cl,5-$CF_3$ | 108.0–112.0 |
| 102 | $CH_3$ | 2,6-$F_2$ | 4- | O | 6-Cl,5-$CF_3$ | |
| 103 | $CH_3$ | 2-Cl,6-F | 4- | O | 4,5-$(CF_3)_2$ | 158.0–160.0 |
| 104 | $CH_3$ | 2,6-$F_2$ | 4- | O | 4,5-$(CF_3)_2$ | |
| 105 | $CH_3$ | 2-Cl,6-F | 4- | O | 6-Cl,4-$CF_3$ | not measurable |
| 106 | $CH_3$ | 2,6-$F_2$ | 4- | O | 6-Cl,4-$CF_3$ | |
| 107 | $CH_3$ | 2-Cl,6-F | 4- | O | 4,6-$(CF_3)_2$ | 125.0–129.0 |
| 108 | $CH_3$ | 2,6-$F_2$ | 4- | O | 4,6-$(CF_3)_2$ | |
| 109 | $CH_3$ | 2-Cl,6-F | 4- | O | 6-$CH_3$,4-$CF_3$ | 98.0–101.0 |
| 110 | $CH_3$ | 2,6-$F_2$ | 4- | O | 6-$CH_3$,4-$CF_3$ | |

TABLE 5

| Compound No. | $R^1$ | $X_n$ | Substitution position | $(A)_k$ | $R^2m$ | Melting point (°C.) or refractive index ($n_D^{20}$) |
|---|---|---|---|---|---|---|
| 111 | $CH_3$ | 2,6-$F_2$ | 3- | — | 5-$CF_3$ | |
| 112 | $CH_3$ | 2,6-$F_2$ | 3- | S | 5-$CF_3$ | |
| 113 | $CH_3$ | 2,6-$F_2$ | 3- | $CH_2$ | 5-$CF_3$ | |
| 114 | $CH_3$ | 2,6-$Cl_2$ | 3- | O | 3-Cl,5-$CF_3$ | |
| 115 | $CH_3$ | 2-Cl | 3- | S | 3-Cl,5-$CF_3$ | |
| 116 | $CH_3$ | 2-Cl,6-F | 3- | S | 3-Cl,5-$CF_3$ | |
| 117 | $CH_3$ | 2,6-$F_2$ | 3- | S | 3-Cl,5-$CF_3$ | |
| 118 | $CH_3$ | 2,6-$Cl_2$ | 3- | S | 3-Cl,5-$CF_3$ | |
| 119 | $CH_3$ | 2-Cl | 3- | $CH_2O$ | 3-Cl,5-$CF_3$ | |
| 120 | $CH_3$ | 2-Cl,6-F | 3- | $CH_2O$ | 3-Cl,5-$CF_3$ | not measurable |
| 121 | $CH_3$ | 2,6-$F_2$ | 3- | $CH_2O$ | 3-Cl,5-$CF_3$ | |
| 122 | $CH_3$ | 2,6-$Cl_2$ | 3- | $CH_2O$ | 3-Cl,5-$CF_3$ | |
| 123 | $CH_3$ | 2-Cl,6-F | 3- | $CH_2O$ | 3,5-$(CF_3)_2$ | |
| 124 | $CH_3$ | 2,6-$F_2$ | 3- | $CH_2O$ | 3,5-$(CF_3)_2$ | |
| 125 | $CH_3$ | 2-Cl,6-F | 3- | $CH_2O$ | 4,5-$(CF_3)_2$ | 72.0–78.0 |
| 126 | $CH_3$ | 2,6-$F_2$ | 3- | $CH_2O$ | 4,5-$(CF_3)_2$ | |
| 127 | $CH_3$ | 2-Cl,6-F | 3- | $CH_2O$ | 4,6-$(CF_3)_2$ | 1.5360 |
| 128 | $CH_3$ | 2,6-$F_2$ | 3- | $CH_2O$ | 4,6-$(CF_3)_2$ | |
| 129 | $CH_3$ | 2-Cl,6-F | 3- | $CH_2O$ | 6-$CH_3$,4-$CF_3$ | |
| 130 | $CH_3$ | 2,6-$F_2$ | 3- | $CH_2O$ | 6-$CH_3$,4-$CF_3$ | |
| 131 | $CH_3$ | 2-Cl,6-F | 3- | $CH_2O$ | 5-Cl | |
| 132 | $CH_3$ | 2,6-$F_2$ | 3- | $CH_2O$ | 5-Cl | |
| 133 | $CH_3$ | 2-Cl,6-F | 3- | $CH_2O$ | 5-$CH_3$ | |
| 134 | $CH_3$ | 2,6-$F_2$ | 3- | $CH_2O$ | 5-$CH_3$ | |
| 135 | $CH_3$ | 2-Cl,6-F | 3- | $CH_2O$ | 3,5-$Cl_2$ | |
| 126 | $CH_3$ | 2,6-$F_2$ | 3- | $CH_2O$ | 3,5-$Cl_2$ | |
| 127 | $CH_3$ | 2-Cl,6-F | 3- | $CH_2O$ | 5-Cl,3-$CF_3$ | |
| 128 | $CH_3$ | 2,6-$F_2$ | 3- | $CH_2O$ | 5-Cl,3-$CF_3$ | |
| 129 | $CH_3$ | 2-Cl,6-F | 3- | $CH_2O$ | 6-Cl,5-$CF_3$ | |

TABLE 6

| Compound No. | $R^1$ | $X_n$ | Substitution position | $(A)_k$ | $R^2m$ | Melting point (°C.) or refractive index ($n_D^{20}$) |
|---|---|---|---|---|---|---|
| 140 | $CH_3$ | 2,6-$F_2$ | 3- | $CH_2O$ | 6-Cl,5-$CF_3$ | |
| 141 | $CH_3$ | 2-Cl,6-F | 3- | $CH_2O$ | 6-Cl,4-$CF_3$ | |

TABLE 6-continued

| Compound No. | $R^1$ | $X_n$ | Substitution position | $(A)_k$ | $R^2m$ | Melting point (°C.) or refractive index ($n_D^{20}$) |
|---|---|---|---|---|---|---|
| 142 | $CH_3$ | 2,6-$F_2$ | 3- | $CH_2O$ | 6-Cl,4-$CF_3$ | |
| 143 | $CH_3$ | 2-Cl,6-F | 3- | O | 3,5-$Cl_2$ | 52.0–56.0 |
| 144 | $CH_3$ | 2,6-$F_2$ | 3- | O | 3,5-$Cl_2$ | |
| 145 | $CH_3$ | 2-Cl,6-F | 4- | $CH_2O$ | 5-Cl | 140.0–145.0 |
| 146 | $CH_3$ | 2,6-$F_2$ | 4- | $CH_2O$ | 5-Cl | |
| 147 | $CH_3$ | 2-Cl,6-F | 4- | $CH_2O$ | 6-Cl | |
| 148 | $CH_3$ | 2,6-$F_2$ | 4- | $CH_2O$ | 6-Cl | |
| 149 | $CH_3$ | 2-Cl,6-F | 4- | $CH_2O$ | 4-$CH_3$ | |
| 150 | $CH_3$ | 2,6-$F_2$ | 4- | $CH_2O$ | 4-$CH_3$ | |
| 151 | $CH_3$ | 2-Cl,6-F | 4- | $CH_2O$ | 5-$CH_3$ | |
| 152 | $CH_3$ | 2,6-$F_2$ | 4- | $CH_2O$ | 5-$CH_3$ | |
| 153 | $CH_3$ | 2-Cl,6-F | 4- | $CH_2O$ | 6-$CH_3$ | |
| 154 | $CH_3$ | 2,6-$F_2$ | 4- | $CH_2O$ | 6-$CH_3$ | |
| 155 | $CH_3$ | 2-Cl,6-F | 4- | $CH_2O$ | 3-$CF_3$ | |
| 156 | $CH_3$ | 2,6-$F_2$ | 4- | $CH_2O$ | 3-$CF_3$ | |
| 157 | $CH_3$ | 2-Cl,6-F | 4- | $CH_2O$ | 4-$CF_3$ | |
| 158 | $CH_3$ | 2,6-$F_2$ | 4- | $CH_2O$ | 4-$CF_3$ | |
| 159 | $CH_3$ | 2-Cl,6-F | 4- | $CH_2O$ | 6-$CF_3$ | |
| 160 | $CH_3$ | 2,6-$F_2$ | 4- | $CH_2O$ | 6-$CF_3$ | |
| 161 | $CH_3$ | 2-Cl | 4- | $CH_2O$ | 3,5-$Cl_2$ | |
| 162 | $CH_3$ | 2-Cl,6-F | 4- | $CH_2O$ | 3,5-$Cl_2$ | 121.0–124.0 |
| 163 | $CH_3$ | 2,6-$F_2$ | 4- | $CH_2O$ | 3,5-$Cl_2$ | |
| 164 | $CH_3$ | 2,6-$Cl_2$ | 4- | $CH_2O$ | 3,5-$Cl_2$ | |
| 165 | $CH_3$ | 2-Cl | 4- | $CH_2O$ | 5-Cl,3-$CF_3$ | |
| 166 | $CH_3$ | 2-Cl,6-F | 4- | $CH_2O$ | 5-Cl,3-$CF_3$ | 89.0–94.0 |
| 167 | $CH_3$ | 2,6-$F_2$ | 4- | $CH_2O$ | 5-Cl,3-$CF_3$ | |
| 168 | $CH_3$ | 2,6-$Cl_2$ | 4- | $CH_2O$ | 5-Cl,3-$CF_3$ | |

TABLE 7

| Compound No. | $R^1$ | $X_n$ | Substitution position | $(A)_k$ | $R^2m$ | Melting point (°C.) or refractive index ($n_D^{20}$) |
|---|---|---|---|---|---|---|
| 169 | $CH_3$ | 2,6-$F_2$ | 3- | $CH_2O$ | 6-Cl,5-$CF_3$ | |
| 170 | $CH_3$ | 2,6-$Cl_2$ | 4- | $CH_2O$ | 3-Cl,5-$CF_3$ | |
| 171 | $CH_3$ | 2-Cl | 4- | $CH_2O$ | 3,5-$(CF_3)_2$ | |
| 172 | $CH_3$ | 2-Cl,6-F | 4- | $CH_2O$ | 3,5-$(CF_3)_2$ | 87.0–91.0 |
| 173 | $CH_3$ | 2,6-$F_2$ | 4- | $CH_2O$ | 3,5-$(CF_3)_2$ | |
| 174 | $CH_3$ | 2,6-$Cl_2$ | 4- | $CH_2O$ | 3,5-$(CF_3)_2$ | |
| 175 | $CH_3$ | 2-Cl | 4- | $CH_2O$ | 6-Cl,5-$CF_3$ | |
| 176 | $CH_3$ | 2-Cl,6-F | 4- | $CH_2O$ | 6-Cl,5-$CF_3$ | 138.0–140.0 |
| 177 | $CH_3$ | 2,6-$F_2$ | 4- | $CH_2O$ | 6-Cl,5-$CF_3$ | |
| 178 | $CH_3$ | 2,6-$Cl_2$ | 4- | $CH_2O$ | 6-Cl,5-$CF_3$ | |
| 179 | $CH_3$ | 2-Cl | 4- | $CH_2O$ | 4,5-$(CF_3)_2$ | |
| 180 | $CH_3$ | 2-Cl,6-F | 4- | $CH_2O$ | 4,5-$(CF_3)_2$ | 113.0–116.0 |
| 181 | $CH_3$ | 2,6-$F_2$ | 4- | $CH_2O$ | 4,5-$(CF_3)_2$ | |
| 182 | $CH_3$ | 2,6-$Cl_2$ | 4- | $CH_2O$ | 4,5-$(CF_3)_2$ | |
| 183 | $CH_3$ | 2-Cl | 4- | $CH_2O$ | 6-Cl,4-$CF_3$ | |
| 184 | $CH_3$ | 2-Cl,6-F | 4- | $CH_2O$ | 6-Cl,4-$CF_3$ | not measureable |
| 185 | $CH_3$ | 2,6-$F_2$ | 4- | $CH_2O$ | 6-Cl,4-$CF_3$ | |
| 186 | $CH_3$ | 2,6-$Cl_2$ | 4- | $CH_2O$ | 6-Cl,4-$CF_3$ | |
| 187 | $CH_3$ | 2-Cl | 4- | $CH_2O$ | 4,6-$(CF_3)_2$ | |
| 188 | $CH_3$ | 2-Cl,6-F | 4- | $CH_2O$ | 4,6-$(CF_3)_2$ | |
| 189 | $CH_3$ | 2,6-$F_2$ | 4- | $CH_2O$ | 4,6-$(CF_3)_2$ | |
| 190 | $CH_3$ | 2,6-$Cl_2$ | 4- | $CH_2O$ | 4,6-$(CF_3)_2$ | |
| 191 | $CH_3$ | 2-Cl | 4- | $CH_2O$ | 6-$CH_3$,4-$CF_3$ | |
| 192 | $CH_3$ | 2-Cl,6-F | 4- | $CH_2O$ | 6-$CH_3$,4-$CF_3$ | |
| 193 | $CH_3$ | 2,6-$F_2$ | 4- | $CH_2O$ | 6-$CH_3$,4-$CF_3$ | |
| 194 | $CH_3$ | 2,6-$Cl_2$ | 4- | $CH_2O$ | 6-$CH_3$,4-$CF_3$ | |
| 195 | $CH_3$ | 2-Cl,6-F | 4- | $CH_2CH_2O$ | 3-Cl,5-$CF_3$ | |
| 196 | $CH_3$ | 2,6-$F_2$ | 4- | $CH_2CH_2O$ | 3-Cl,5-$CF_3$ | |
| 197 | $CH_3$ | 2-Cl,6-F | 4- | $CH_2CH_2O$ | 3,5-$(CF_3)_2$ | |

TABLE 8

| Compound No. | $R^1$ | $X_n$ | Substitution position | $(A)_k$ | $R^2{}_m$ | Melting point (°C.) or refractive index ($n_D{}^{20}$) |
|---|---|---|---|---|---|---|
| 198 | $CH_3$ | 2,6-$F_2$ | 4- | $CH_2CH_2O$ | 3,5-$(CF_3)_2$ | |
| 199 | $CH_3$ | 2-Cl,6-F | 4- | $CH_2CH_2O$ | 6-Cl,5-$CF_3$ | |
| 200 | $CH_3$ | 2,6-$F_2$ | 4- | $CH_2CH_2O$ | 6-Cl,5-$CF_3$ | |
| 201 | $CH_3$ | 2-Cl,6-F | 4- | $CH_2CH_2O$ | 5-Cl,3-$CF_3$ | |
| 202 | $CH_3$ | 2,6-$F_2$ | 4- | $CH_2CH_2O$ | 5-Cl,3-$CF_3$ | |
| 203 | $CH_3$ | 2-Cl,6-F | 4- | $CH_2CH_2O$ | 4,5-$(CF_3)_2$ | |
| 204 | $CH_3$ | 2,6-$F_2$ | 4- | $CH_2CH_2O$ | 4,5-$(CF_3)_2$ | |
| 205 | $CH_3$ | 2-Cl,6-F | 4- | $CH_2CH_2O$ | 6-Cl,4-$CF_3$ | |
| 206 | $CH_3$ | 2,6-$F_2$ | 4- | $CH_2CH_2O$ | 6-Cl,4-$CF_3$ | |
| 207 | $CH_3$ | 2-Cl,6-F | 4- | $CH_2CH_2O$ | 4,6-$(CF_3)_2$ | |
| 208 | $CH_3$ | 2,6-$F_2$ | 4- | $CH_2CH_2O$ | 4,6-$(CF_3)_2$ | |
| 209 | $CH_3$ | 2-Cl,6-F | 4- | $CH_2CH_2O$ | 6-$CH_3$,4-$CF_3$ | |
| 210 | $CH_3$ | 2,6-$F_2$ | 4- | $CH_2CH_2O$ | 6-$CH_3$,4-$CF_3$ | |
| 211 | $CH_3$ | 2-Cl,6-F | 4- | $CH_2CH_2O$ | 3,5-$Cl_2$ | |
| 212 | $CH_3$ | 2,6-$F_2$ | 4- | $CH_2CH_2O$ | 3,5-$Cl_2$ | |
| 213 | $CH_3$ | 2-Cl,6-F | 4- | S | 3,5-$Cl_2$ | |
| 214 | $CH_3$ | 2,6-$F_2$ | 4- | S | 3,5-$Cl_2$ | |
| 215 | $CH_3$ | 2-Cl,6-F | 4- | S | 5-Cl,3-$CF_3$ | |
| 216 | $CH_3$ | 2,6-$F_2$ | 4- | S | 5-Cl,3-$CF_3$ | |
| 217 | $CH_3$ | 2-Cl,6-F | 4- | S | 3,5-$(CF_3)_2$ | |
| 218 | $CH_3$ | 2,6-$F_2$ | 4- | S | 3,5-$(CF_3)_2$ | |
| 219 | $CH_3$ | 2-Cl,6-F | 4- | S | 6-Cl,5-$CF_3$ | |
| 220 | $CH_3$ | 2,6-$F_2$ | 4- | S | 6-Cl,5-$CF_3$ | |
| 221 | $CH_3$ | 2-Cl,6-F | 4- | S | 4,5-$(CF_3)_2$ | |
| 222 | $CH_3$ | 2,6-$F_2$ | 4- | S | 4,5-$(CF_3)_2$ | |
| 223 | $CH_3$ | 2-Cl,6-F | 4- | S | 4,6-$(CF_3)_2$ | |
| 224 | $CH_3$ | 2,6-$F_2$ | 4- | S | 4,6-$(CF_3)_2$ | |
| 225 | $CH_3$ | 2-Cl,6-F | 4- | $CH_2CH_2$ | 3-Cl,5-$CF_3$ | 1.5730 |
| 226 | $CH_3$ | 2-Cl,6-F | 4- | $CH_2O$ | 6-Cl,3-$CF_3$ | 113.0–116.0 |
| 227 | $CH_3$ | 2-Cl,6-F | 4- | $OCH_2$ | 4-Cl | |
| 228 | $CH_3$ | 2-Cl,6-F | 4- | $CH_2OCH_2$ | H | |

The compounds according to the invention can be produced by the following methods. However, it is not intended to restrict the invention to these methods.

Production Method A

The compound of the general formula [I] according to the invention can be obtained by reacting an alkyl N-acyl(thio)imidate derivative of a general formula [II] with a hydrazine derivative of a general formula [III] in an inert solvent according to the following reaction formula (1):

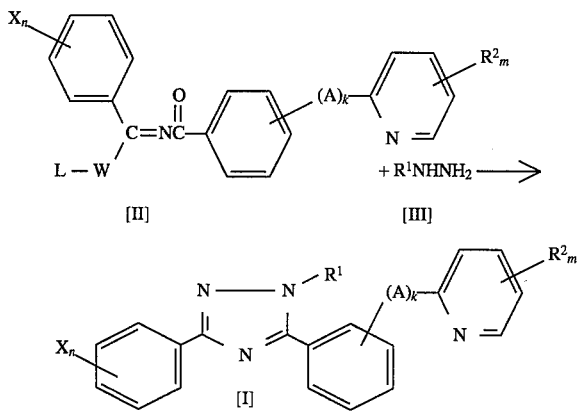

(wherein W is a sulfur atom or an oxygen atom, L is an alkyl group having a carbon number of 1–4 and $R^1$, X, n, A, $R^2$, m and k have the same meaning as mentioned above).

As the solvent, use may be made of any solvent not obstructing the reaction, which includes, for example, an alcohol such as methanol, ethanol or the like; an ether such as diethyl ether, tetrahydrofuran, dioxane, diglyme or the like; an aromatic hydrocarbon such as benzene, toluene, chlorobenzene or the like; an aliphatic hydrocarbon such as pentane, hexane, petroleum ether of the like; a halogenated hydrocarbon such as dichloromethane, dichloroethane, chloroform, carbon tetrachloride or the like; a nitrile such as acetonitrile or the like; an aprotic polar solvent such as N,N-dimethylformamide, N,N-dimethylacetamide, dimethylsulfoxide or the like; water and a mixture thereof.

In general, the compound of the general formula [III] is used in an amount of 1.0–5.0 moles per 1 mole of the compound of the general formula [II].

The reaction temperature is optional within a range of 0° C. to a boiling point of the solvent, but is preferably 0° C.–50° C. The reaction time is dependent upon the kind of compounds used, but is usually 1–72 hours.

A concrete example of this reaction is disclosed, for example, in Synthesis, page 483 (1983).

The compound of the general formula [II] as a starting material can be produced by the following method.

Production Method B

The compound of the general formula [II] can be obtained by reacting compounds of the general formulae [IV] and [V] in an inert solvent in the presence of a base according to the following reaction formula (2):

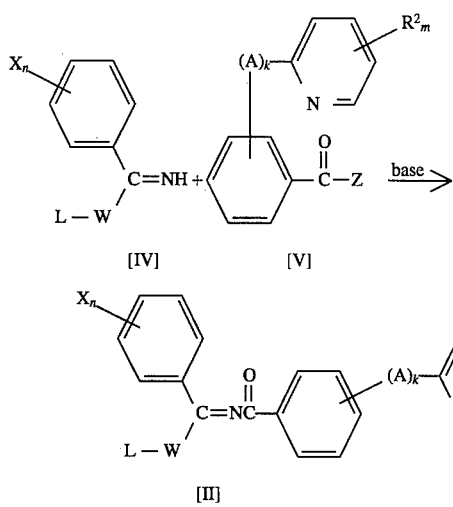

[IV]   [V]

[II]

(wherein a derivative of the general formula [IV] may be an acid addition salt (e.g. a salt with boron tetrafluoride, hydrogen chloride, hydrogen bromide, hydrogen iodide or the like), Z is a halogen atom, and L, W, X, n, A, k, $R^2$ and m have the same meaning as mentioned above).

As the base, use may be made of an inorganic base such as sodium carbonate, potassium carbonate, sodium hydrogen carbonate, sodium hydroxide, potassium hydroxide or the like; and an organic base such as diethylamine, triethylamine, diisopropylethylamine, pyridine, 4-N,N-dimethylamino pyridine or the like.

As the solvent, use may be made of a ketone such as acetone, methyl ethyl ketone or the like; an ether such as diethyl ether, tetrahydrofuran, dioxane, diglyme or the like; an aromatic hydrocarbon such as benzene, toluene, chlorobenzene or the like; an aliphatic hydrocarbon such as pentane, hexane, petroleum ether or the like; a halogenated hydrocarbon such as dichloromethane, dichloroethane, chloroform, carbon tetrachloride or the like; a nitrile such as acetonitrile or the like; an aprotic polar solvent such as N,N-dimethylformamide, N,N-dimethylacetamide, dimethylsulfoxide or the like; and a mixture thereof.

In general, the compound of the general formula [V] is used in an amount of 0.8–1.3 moles per 1 mole of the compound of the general formula [IV]. The amount of the base used is 1.0–2.0 moles per 1 mole of the compound of the general formula [IV].

The reaction time is dependent upon the kind of the compounds used, but is usually within a range of 1–24 hours. The reaction temperature is within a range of 0° C. to a boiling point of the solvent.

Production Method C

The compound of the general formula [I] according to the invention can be obtained by reacting an N-(phenylsulfonyl) benzohydrazonoyl chloride derivative of a general formula [VI] with a benzonitrile derivative of a general formula [VII] in an inert solvent in the presence of Lewis acid according to the following reaction formula (3):

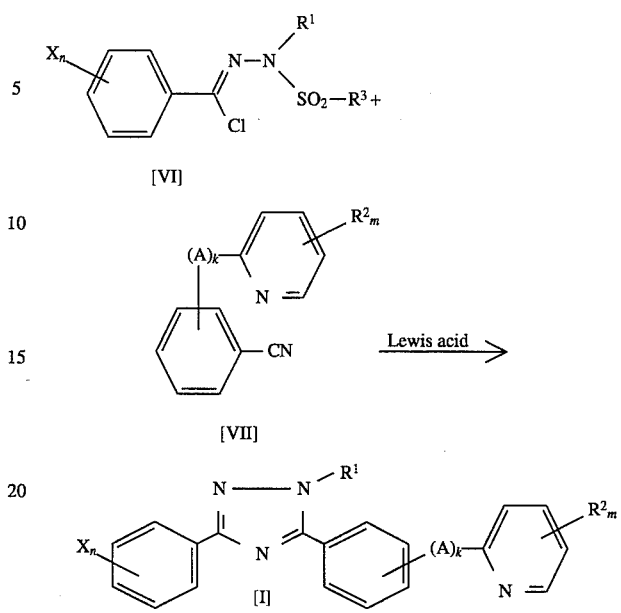

[VI]

[VII]

[I]

(wherein $R^1$, X, n, A, k, $R^2$ and m have the same meaning as mentioned above, and $R^3$ is benzene or benzene substituted with an alkyl group having a carbon number of 1–4).

As the solvent, use may be made of any solvent not obstructing the reaction, which includes, for example, an ether such as diethyl ether, tetrahydrofuran, dioxane, diglyme or the like; an aromatic hydrocarbon such as benzene, toluene, chlorobenzene, dichlorobenzene or the like; an aliphatic hydrocarbon such as pentane, hexane, petroleum ether or the like; a halogenated hydrocarbon such as dichloromethane, dichloroethane, chloroform, carbon tetrachloride or the like; a non-protonic polar solvent such as nitrobenzene, N,N-dimethylformamide, N,N-dimethylacetamide, dimethylsulfoxide or the like; and a mixture thereof.

As the Lewis acid, use may be made of aluminum bromide, aluminum chloride, ferric chloride, boron trifluoride, titanium tetrachloride and the like.

In general, the amount of the compound of the general formula [VII] used is 1.0–2.0 moles per 1 mole of the compound of the general formula [VI], and the amount of the Lewis acid used is 1.0–2.0 moles per 1 mole of the compound of the general formula [VI].

The reaction temperature is optionally within a range of 0° C. to a boiling point of the solvent, but is preferably within a range of 50°–180° C. The reaction time is dependent upon the kind of the compounds used, but is usually within a range of 15 minutes to 8 hours.

A concrete example of this reaction is disclosed, for example, in BULLETIN of the CHEMICAL SOCIETY of JAPAN, vol. 56, pages 545–548 (1983).

Production Method D

The compound of the general formula [I] according to the invention can be obtained by reacting an N-(phenylsulfonyl) benzamidrazone derivative of a general formula [VIII] with a benzoylhalide derivative of the general formula [V] in the absence of a solvent or in the presence of an inert solvent according to the following reaction formula (4):

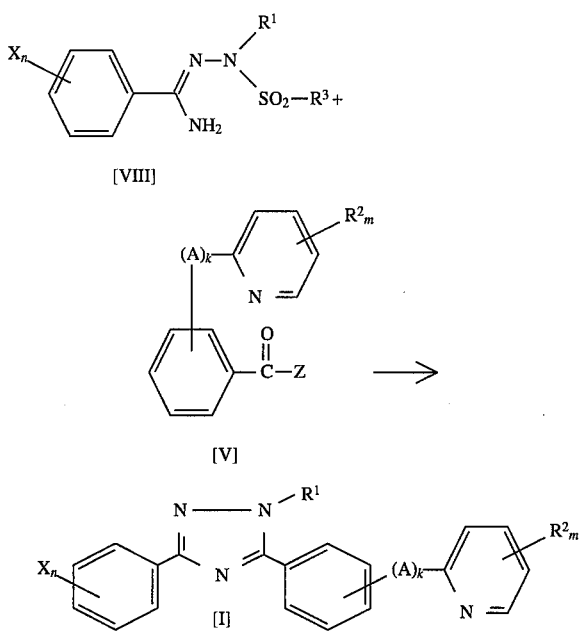

(wherein $R^1$, $R^3$, X, n, Z, A, k, $R^2$ and m have the same meaning as mentioned above).

As the solvent, use may be made of any solvent not obstructing the reaction, which includes, for example, an ether such as diethyl ether, tetrahydrofuran, dioxane, diglyme or the like; an aromatic hydrocarbon such as benzene, toluene, chlorobenzene or the like; an aliphatic hydrocarbon such as pentane, hexane, petroleum ether or the like; a halogenated hydrocarbon such as dichloromethane, dichloroethane, chloroform, carbon tetrachloride or the like; an aprotic polar solvent such as N,N-dimethylformamide, N,N-dimethylacetamide, dimethylsulfoxide, 1-methyl-2-pyrolidinone or the like; and a mixture thereof.

In general, the amount of the compound of the general formula [V] used is 1.0–2.0 moles per 1 mole of the compound of the general formula [VIII].

The reaction temperature is optionally within a range of 0° C. to a boiling point of the solvent, but is preferably within a range of 50°–250° C. The reaction time is dependent upon the kind of the compounds used, but is usually within a range of 30 minutes to 5 hours.

A concrete example of this reaction is disclosed, for example, in BULLETIN of the CHEMICAL SOCIETY of JAPAN, vol. 56, page 548 (1983).

The compound of the general formula [VIII] as a starting material can be produced by the following method.

Production Method E

The compound of the general formula [VIII] can be obtained by reacting the compound of the general formula [VI] with ammonia gas in an inert solvent according to the following reaction formula (5):

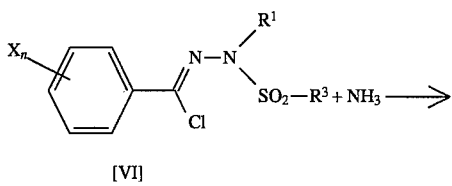

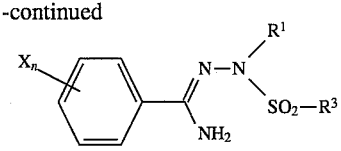

(wherein $R^1$, $R^3$, X and n have the same meaning as mentioned above).

As the solvent, use may be made of any solvent not obstructing the reaction, which includes, for example, an ether such as diethyl ether, tetrahydrofuran, dioxane, diglyme or the like; an aromatic hydrocarbon such as benzene, toluene, chlorobenzene or the like; an aliphatic hydrocarbon such as pentane, hexane, petroleum ether or the like; a halogenated hydrocarbon such as dichloromethane, dichloroethane, chloroform, carbon tetrachloride, dichlorobenzene or the like; an aprotic polar solvent such ass N,N-dimethylformamide, N,N-dimethylacetamide, dimethylsulfoxide or the like; and a mixture thereof.

In general, the amount of ammonia gas used is 5.0–10.0 moles per 1 mole of the compound of the general formula [VI].

The reaction temperature is optionally within a range of 0° C. to a boiling point of the solvent, but is preferably within a range of 20°–150° C. The reaction time is dependent upon the kind of the compounds used, but is usually within a range of 1–24 hours.

A concrete example of this reaction is disclosed, for example, in BULLETIN of the CHEMICAL SOCIETY of JAPAN, vol. 56, pages 545–548 (1983).

Production Method F

The compound of the general formula [I-1] according to the invention can be obtained by reacting compounds of general formulae [IX] and [X] in an inert solvent in the presence of the base according to the following reaction formula (6):

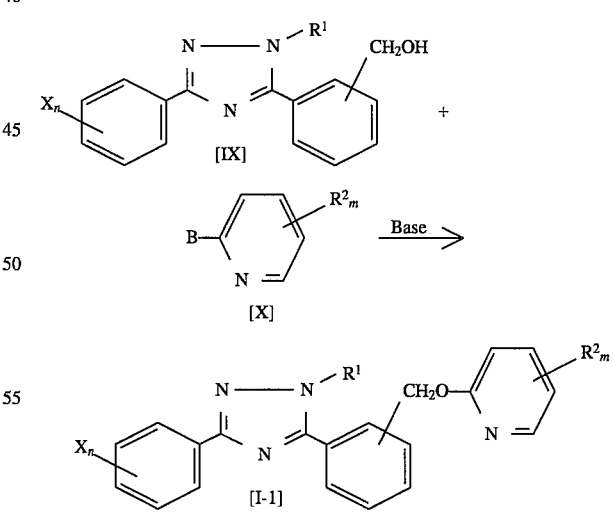

(wherein B is a halogen atom or $R^3$—$SO_3$— group and $R^1$, $R^2$, $R^3$, X, m and n have the same meaning as mentioned above).

As the base, use may be made of an inorganic base such as sodium carbonate, potassium carbonate, sodium hydrogen carbonate, sodium hydroxide, potassium hydroxide or the like; a metal hydride such as sodium hydride, potassium hydride or the like; and an organic base such as triethylamine, pyridine or the like.

As the solvent, use may be made of a ketone such as acetone, methyl ethyl ketone or the like; an ether such as diethyl ether, tetrahydrofuran, dioxane, diglyme or the like; an aromatic hydrocarbon such as benzene, toluene, chlorobenzene or the like; an aliphatic hydrocarbon such as pentane, hexane, petroleum ether or the like; a halogenated hydrocarbon such as dichloromethane, dichloroethane, chloroform, carbon tetrachloride or the like; a nitrile such as acetonitrile or the like; an aprotic polar solvent such as N,N-dimethylformamide, N,N-dimethylacetamide, dimethylsulfoxide or the like; and a mixture thereof.

In general, the compound of the general formula [X] is used in an amount of 1.0–2.0 moles per 1 mole of the compound of the general formula [IX]. The amount of the base used is 1.0–2.0 moles per 1 mole of the compound of the general formula [IX].

The reaction time is dependent upon the kind of the compounds used, but is usually within a range of 1–24 hours. The reaction temperature is within a range of –20° C. to a boiling point of the solvent.

The compound of the general formula [IX] as a starting material can be produced by the following method.

Production Method G

The compound of the general formula [IX] can be obtained by reacting a triazole derivative of a general formula [XII] with a halogenating agent in a solvent, reacting the resulting compound of a general formula [XIII] with an acetoxylating agent in a solvent and then reacting the resulting compound of a general formula [XIX] with acid or alkali in a solvent according to the following reaction formula (7):

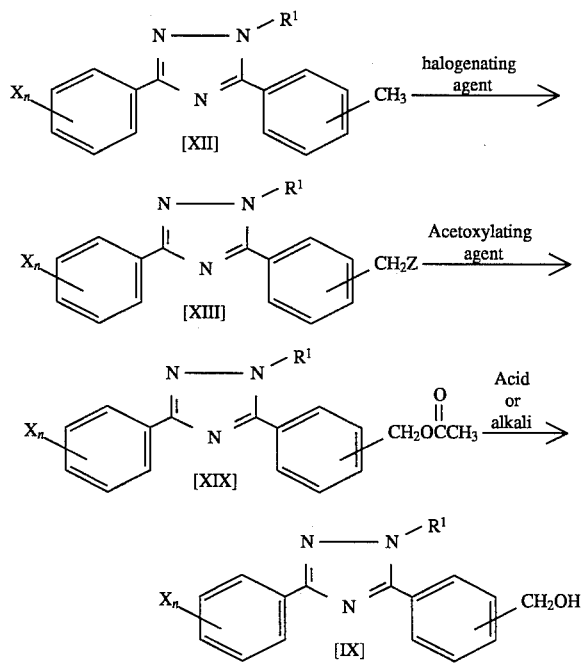

(wherein $R^1$, X, Z and n have the same meaning as mentioned above).

As the halogenating agent, use may be made of N-chlorosuccinimide, N-bromosuccinimide, N-bromophthalimide and the like. As the solvent, mention may be made of dichloromethane, dichloroethane, chloroform, carbon tetrachloride and the like. In this reaction, benzoyl peroxide, azobisisobutylnitrile or the like is required to be added in a catalytic amount as a radical initiator.

As the acetoxylating agent, use may be made of lithium acetate, sodium acetate, potassium acetate, calcium acetate and the like. As the acid, use may be made of inorganic acid such as hydrogen chloride, sulfuric acid or the like; a Lewis acid such as aluminum bromide, aluminum chloride or the like. In this case, as the solvent, use may be made of a ketone such as acetone, methyl ethyl ketone or the like; an ether such as diethyl ether, tetrahydrofuran, dioxane, dimethoxyethane or the like; an aromatic hydrocarbon such as benzene, toluene or the like; an aliphatic hydrocarbon such as pentane, hexane, petroleum ether or the like; a halogenated hydrocarbon such as dichloromethane, dichloroethane, carbon tetrachloride or the like; a nitrile such as acetonitrile or the like.

As the alkali, use may be made of sodium hydroxide solution, potassium hydroxide solution, sodium carbonate solution, potassium carbonate solution or the like. In this case, as the solvent, use may be made of an alcohol such as methanol, ethanol or the like; a ketone such as acetone, methyl ethyl ketone or the like; an ether such as tetrahydrofuran, dioxane, dimethoxyethane or the like; a nitrile such as acetonitrile or the like.

Production Method H

The compound of the general formula [I-2] according to the invention can be obtained by reacting a compound of a general formula [XV] with the compound of the general formula [X] in an inert solvent in the presence of the base according to the following reaction formula (8):

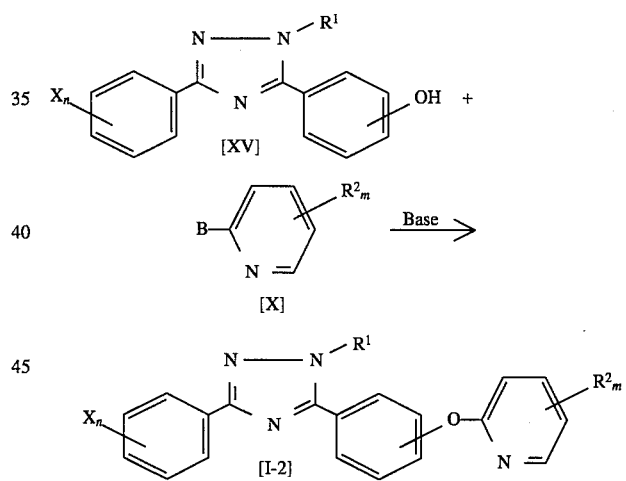

(wherein $R^1$, $R^2$, X, n, B and m have the same meaning as mentioned above).

As the base, use may be made of an inorganic base such as sodium carbonate, potassium carbonate, sodium hydrogen carbonate, sodium hydroxide, potassium hydroxide or the like; a metal hydride such as sodium hydride, potassium hydride or the like; and an organic base such as triethylamine, pyridine or the like.

As the solvent, use may be made of a ketone such as acetone, methyl ethyl ketone or the like; an ether such as diethyl ether, tetrahydrofuran, dioxane, diglyme or the like; an aromatic hydrocarbon such as benzene, toluene, chlorobenzene or the like; an aliphatic hydrocarbon such as pentane, hexane, petroleum ether or the like; a halogenated hydrocarbon such as dichloromethane, dichloroethane, chloroform, carbon tetrachloride or the like; a nitrile such as acetonitrile or the like; an aprotic polar solvent such as N,N-dimethylformamide, N,N-dimethylacetamide, dimethylsulfoxide or the like; and a mixture thereof.

In general, the compound of the general formula [X] is used in an amount of 1.0–2.0 moles per 1 mole of the compound of the general formula [XV]. The amount of the base used is 1.0–2.0 moles per 1 mole of the compound of the general formula [XV].

The reaction time is dependent upon the kind of the compounds used, but is usually within a range of 1–24 hours. The reaction temperature is within a range of −20° C. to a boiling point of the solvent.

The compound of the general formula [XV] as a starting material can be produced by the following method.

Production Method I

The compound of the general formula [XV] can be obtained by reacting a compound of a general formula [XVII] with Lewis acid in an inert solvent according to the following reaction formula (9):

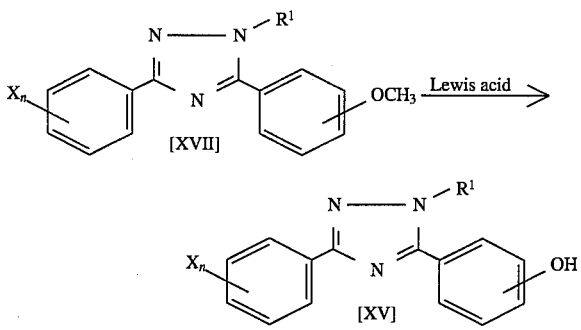

(wherein $R^1$, X and n have the same meaning as mentioned above).

As the Lewis acid, use may be made of aluminum bromide, aluminum chloride, ferric chloride, boron trifluoride, titanium tetrachloride and the like.

As the solvent, use may be made of any solvent not obstructing the reaction, which includes, for example, an ether such as diethyl ether, tetrahydrofuran, dioxane, diglyme or the like; an aromatic hydrocarbon such as benzene, toluene, chlorobenzene, dichlorobenzene or the like; an aliphatic hydrocarbon such as pentane, hexane, petroleum ether or the like; a halogenated hydrocarbon such as dichloromethane, dichloroethane, chloroform, carbon tetrachloride or the like; an aprotic polar solvent such as nitrobenzene, N,N-dimethylformamide, N,N-dimethylacetamide, dimethylsulfoxide or the like; and a mixture thereof.

In general, the Lewis acid is used in an amount of 1.0–5.0 moles per 1 mole of the compound of the general formula [XVII]. The reaction time is dependent upon the kind of the compounds used, but is usually within a range of 1–24 hours. The reaction temperature is within a range of −20° C. to a boiling point of the solvent.

The invention will be described concretely with reference to the following examples, formulation examples and test examples.

EXAMPLE 1

Production of 5-[4-(3-chloror-5-trifluoromethyl-2-pyridyloxymethyl)phenyl]-3-(2,6-difluorophenyl)-1-methyl-1H-1,2,4-triazole (Compound No. 98)

In 50 ml of toluene are dissolved 1.75 g of ethyl 2,6-difluorobenzimidate and 0.87 g of triethylamine, to which is added dropwise a solution of 3.0 g of 4-(3-chloro-5-trifluoromethyl-2-pyridyloxymethyl)-benzoyl chloride in toluene at room temperature. The resulting mixture is heated under reflux for 3 hours. After the reaction solution is cooled and extracted with 50 ml of toluene, the extract is washed with a diluted hydrochloric acid solution and further with a saline solution, and then dried over anhydrous magnesium sulfate.

The extract is added with 0.6 g of monomethylhydrazine and heated under reflux for 1 hour. After the completion of the reaction, the reaction solution is cooled, washed with a diluted hydrochloric acid solution and further with a saline solution and dried over anhydrous magnesium sulfate and the solvent is distilled off under a reduced pressure. The resulting concentrate is purified by a silica gel column chromatography using a mixed solution of hexane and ethyl acetate as a developing solvent to obtain 0.53 g of a given compound (melting point: 132.0°–136.0° C.).

NMR data (60 MHz, CDCl$_3$ solvent, δ value) 8.23–6.8 ppm (m, 9H) 5.53 ppm (s, 2H) 4.03 ppm (s, 3H)

EXAMPLE 2

Production of 3-(2-chloro-6-fluorophenyl)-5-[4-(3-chloro-5-trifluoromethylpyridin-2-yloxy)phenyl]-1-methyl-1H-1,2,4-triazole (Compound No. 6)

A mixture of 1.3 g of N-methyl-N-phenylsulfonyl-2-chloro-6-fluorobenzohydrazonoyl chloride, 1.0 g of 4-(3-chloro-5-trifluoromethylpyridin-2-yloxy)benzonitrile, 0.5 g of anhydrous aluminum chloride and 3 ml of o-dichlorobenzene is stirred in an oil bath at a temperature of 140° C. for 30 minutes. After the cooling, the mixture is dissolved in 100 ml of chloroform and washed with a diluted hydrochloric acid solution, a diluted sodium hydroxide solution and a saline solution in this order. The chloroform layer is dried over anhydrous magnesium sulfate and the solvent is distilled off under a reduced pressure. The resulting concentrate is purified by a silica gel column chromatography using a mixed solution of hexane and ethyl acetate as a developing solvent to obtain 0.7 g of a given compound (refractive index $n^{20}_D$: not measurable).

NMR data (60 MHz, CDCl$_3$ solvent, δ value) 4.07 ppm (s, 3H) 6.75–8.58 ppm (m, 9H)

EXAMPLE 3

Production of 3-(2-chloro-6-fluorophenyl)-1-methyl-5-[4-(5-trifluoromethylpyridin-2-yloxymethyl)phenyl]-1H-1,2,4-triazole (Compound No. 87)

A mixture of 3.6 g of N-methyl-N-(p-toluene-sulfonyl)-2-chloro-6-fluorobenzamidrazone and 3.2 g of 4-(5-trifluoromethylpyridin-2-yloxymethyl)benzoyl chloride is stirred in an oil bath at a temperature of 170°–180° C. for 4 hours. After, the cooling, the mixture is added with water and extracted with ethylacetate. The extract is washed with water and dried over anhydrous magnesium sulfate and the solvent is distllied off under a reduced pressure. The resulting concentrate is purified by a silica gel column chromatography using a mixed solution of hexane and ethyl acetate as a developing solvent to obtain 1.4 g of a given compound (refractive index $n^{20}_D$: 1.5859).

NMR data (60 MHz, CDCl$_3$ solvent, δ value) 4.03 ppm (s, 3H) 5.48 ppm (s, 2H) 6.77–8.40 ppm (m, 10H)

EXAMPLE 4

Production of 3-(2-chloro-6-fluorophenyl)-5-[4-(3-chloro-5-trifluoromethylpyridin-2-yloxymethyl)phenyl]-1-methyl-1H-1,2,4-triazole (Compound No. 97)

To 4.4 g of 60% sodium hydride washed with hexane is added 200 ml of dimethoxyethane, which is cooled to −5° C. To the resulting mixture is added dropwise a solution of 32.0 g of 3-(2-chloro-6 -fluorophenyl)-5-(4-hydroxymethylphenyl)-1-methyl-1H-1,2,4-triazole in 10 ml of dimethoxyethane, which is stirred for 30 minutes. To the resulting reaction solution is added dropwise 24.0 g of 2,3-dichloro-5-trifluoromethylpyridine at −5° C. to −3° C. and the reaction is further continued for 1 hour. After the completion of the reaction, the reaction solution is turned to room temperature, added to water and extracted with ether. The extract is washed with water and dried over anhydrous magnesium sulfate and the solvent is distilled off under a reduced pressure. The resulting concentrate is crystallized by adding hexane to obtain 46 g of a crude crystal. Then, the crystal is recrystallized with a mixed solution of ethanol and n-hexane (3:7) to obtain 30 g of a given compound (melting point: 73.0°–75.0° C.).

EXAMPLE 5

Production of 3-(2-chloro-6-fluorophenyl)-5-[4-(3-chloro-5-trifluoromethylpyridin-2-yloxy)phenyl]-1-methyl-1H-1,2,4-triazole (Compound No. 6)

To 10 ml of dimethylformamide are added 0.6 g of 3-(2-chloro-6-fluorophenyl)-5-(4-hydroxyphenyl)-1-methyl-1H-1,2,4-triazole, 0.45 g of 2,3-dichloro-5-trifluoropyridine and 0.3 g of potassium carbonate, which are heated under reflux for 3 hours. After the cooling, the mixture is added with water and extracted with ethylacetate. The resulting organic layer is washed with water and dried over anhydrous magnesium sulfate and the solvent is distilled off under a reduced pressure. The resulting concentrate is purified by a silica gel column chromatography using a mixed solution of hexane and ethyl acetate (4:1) as a developing solvent to obtain 0.6 g of a given compound (melting point: not measurable).

NMR data (60 MHz, CDCl$_3$ solvent, δ value) 4.06 ppm (s, 3H) 6.82–8.50 ppm (m, 9H)

EXAMPLE 6 production of N-methyl-N-phenylsulfonyl-2-chlorobenzamidrazone

In 100 ml of N,N-dimethylformamide is dissolved 17.2 g of N-methyl-N-phenylsulfonyl-2-chlorobenzhydrazonoyl chloride, which is stirred at 60°–70° C. for 3 hours while introducing ammonia gas thereinto. After the cooling, the reaction solution is dissolved in 500 ml of ethyl acetate, washed with water, dried over anhydrous magnesium sulfate and concentrated under a reduced pressure. The resulting crystal is washed with n-hexane to obtain 15.4 g of a given compound (melting point: 94.0°–96.0° C.).

NMR data (60 MHz, CDCl$_3$ solvent, δ value) 2.75 ppm (s, 3H) 7.10–8.00 ppm (m, 9H)

EXAMPLE 7

Production of 3-(2-chloro-6-fluorophenyl)-5-(4-hydroxymethylphenyl)-1-methyl-1H-1,2,4-triazole A mixture of 51 g of 3-(2-chloro-6 -fluorophenyl)-5-(4-methylphenyl)-1-methyl-1H-1,2,4 -triazole, 33 g of N-bromosuccinimide, 1.0 g of benzoyl peroxide and 300 ml of carbon tetrachloride is heated under reflux for 5 hours. After the cooling, the solvent is distilled off to obtain 130 g of a crude product of 5-(4-bromomethylphenyl)-3-(2-chloro-6 -fluorophenyl)-1-methyl-1H-1,2,4-triazole. This product is dissolved in 300 ml of N,N-dimethylformamide and added with 47 g of potassium acetate, which is stirred at 120° C. for 6 hours. After the completion of the reaction, the resulting product is poured in a great amount of water and extracted with ethyl acetate. The extract is washed with water and dried over anhydrous magnesium sulfate and the solvent is distilled off under a reduced pressure to obtain 5-(4-acetoxymethylphenyl)-3-(2 -chloro-6-fluorophenyl)1-methyl-1H-1,2,4-triazole. This compound is dissolved in 300 ml of ethanol and added with 200 ml of 10% sodium hydroxide solution, which is heated under reflux for 1 hour. After the completion of the reaction, ethanol is distilled off under a reduced pressure and the residue is poured into water and extracted with ethyl acetate. The extract is washed with water, dried over anhydrous magnesium sulfate and concentrated under a reduced pressure to obtain 88 g of a given crude crystal. This crystal is recrystallized with ethanol to obtain 54.3 g of the given compound (melting point: 128.0°–130.0° C.).

EXAMPLE 8

Production of 3-(2-chloro-6-fluorophenyl)-5-(4-hydroxyphenyl)-1-methyl-1H-1,2,4-triazole A mixture of 11.9 g of 3-(2-chloro-6 -fluorophenyl)-5-(4-methoxyphenyl)-1-methyl-1H-1,2,4 -triazole, 15.0 g of aluminum chloride and 200 ml of benzene is heated under reflux for 1.5 hours. After the cooling, the solvent is distilled off and the residue is poured into water and extracted with ethyl acetate. The extract is washed with water and dried over anhydrous magnesium sulfate and the solvent is distilled off under a reduced pressure. The residue is washed with hexane to obtain 10.2 g of a given compound (melting point: 236.0°–240.0° C.).

NMR data (60 MHz, CDCl$_3$ solvent, δ value) 4.02 ppm (s, 3H) 6.60–7.80 ppm (m, 7H) 9.36–9.56 ppm (br, 1H)

The insecticide and acaricide according to the invention contain the triazole derivative represented by the general formula [I] as an active ingredient.

When the triazole compounds according to the invention are used as an active ingredient for insecticides and acaricides, these compounds themselves may be used alone, or may be compounded with a carrier, a surfactant, a dispersing agent, an adjuvant or the like usually used in the formulation to form dusts, wettable powder, emulsion, fine powder, granules or the like.

As the carrier used in the formulation, mention may be made of a solid carrier such as zeeklite, talc, bentonite, clay, kaolin, diatomaceous earth, white carbon, vermiculite, calcium hydroxide, quartz sand, ammonium sulfate, urea or the like; and a liquid carrier such as isopropyl alcohol, xylene, cyclohexane, methylnaphthalene or the like.

As the surfactant and dispersing agent, mention may be made of a metal salt of alkylbenzene sulfonic acid, a metal salt of dinaphtylmethane disulfonic acid, a sulfuric acid ester of alcohol, alkylarylsulfonate, lignin sulfonate, polyoxyethylene glycol ether, polyoxyethylene alkylaryl ether, polyoxyethylene sorbitan monoalkylate and the like.

As the adjuvant, mention may be made of carboxymethylcellulose, polyethylene glycol, gum arabi and the like.

In use, the compound according to the invention is directly applied or sprayed by diluting to a proper concentration.

The insecticide and acaricide according to the invention may be used by spraying onto stem and leaves, by applying to soil, by applying to a nursery box, by spraying onto water surface or the like.

In the formulation, the amount of the active ingredient used may be selected in accordance with the use purpose, but it is properly selected within a range of 0.05–20% by weight, preferably 0.1–10% by weight in case of the dusts or granules. In case of the emulsion or wettable powder, the amount of the active ingredient is properly selected within a range of 0.5–80% by weight, preferably 1–60% by weight.

The amount of the insecticide and acaricide applied is dependent upon the kind of the compound used as an active ingredient, injurious insect to be controlled, tendency and degree of insect injury, environmental condition, kind of formulation used and the like. When the insecticide and acaricide according to the invention are directly used as dusts or granules, the amount of the active ingredient is properly selected within a range of 0.05–5 kg, preferably 0.1–1 kg per 10 are. Furthermore, when they are used in form of a liquid as emulsion or wettable powder, the amount of the active ingredient is properly selected within a range of 0.1–5000 ppm, preferably 1–1000 ppm.

Moreover, the insecticide and acaricide according to the invention may be used by mixing with other insecticide, fungicide, fertilizer, plant growth regulator and the like.

The formulation will concretely be described with respect to typical examples. In this case, the kind of the compounds and additives and the compounding ratio are not limited to these examples and may be varied within wide ranges. Moreover, % is by weight otherwise specified.

Formulation Example 1

Emulsion

An emulsion is prepared by uniformly dissolving 30% of compound No. 10, 20% of cyclohexanone, 11% of polyoxyethylene alkylaryl ether, 4% of calcium alkylbenzenesulfonate and 35% of methylnaphthalene.

Formulation Example 2

Wettable powder

A wettable powder is prepared by uniformly mixing and pulverizing 40% of compound No. 80, 15% of diatomaceous earth, 15% of clay, 25% of white carbon, 2% of sodium dinaphthylmethane disulfonate and 3% of sodium lignin sulfonate.

Formulation Example 3

Dust

A dust is prepared by uniformly mixing and pulverizing 2% of compound No. 48, 5% of diatomaceous earth and 93% of clay.

Formulation Example 4

Granules

A mixture of 5% of compound No. 22, 2% of sodium salt of lauryl alcohol sulfuric acid ester, 5% of sodium lignin sulfonate, 2% of carboxymethyl cellulose and 86% of clay is uniformly pulverized and added with 20 parts of water based on 100 parts of the mixture, which is kneaded, shaped into granules of 14–32 mesh through an extrusion type granulating machine and dried to form granules.

The triazole derivatives according to the invention are effective to control planthoppers such as brown planthopper, white-backed planthopper, small brown planthopper and the like; leafhoppers such as green rice leafhopper, tea green leafhopper and the like; aphids such as cotton aphid, green peach aphid, cabbage aphid and the like; whiteflies such as greenhouse whitefly and the like; hemipteran injurious insects such as mulberry scale, corbett rice bug and the like; lepidopteran injurious insects such as diamond-back moth, lima-bean cutworm, tobacco cutworm and the like; dipteran injurious insects such as house maggot, mosquito and the like; elytron injurious insects such as rice plant weevil, soy bean weevil, cucrbit leaf beetle and the like; orthopteran injurious insects such ass american cockroach, stem fly and the like; mites such as two-spotted spider mite, kanzawa spider mite, citrus red mite and the like; and mites having an increased resistance to organotin, synthesized pyrethroid and organophosphorus chemicals.

Particularly, they develop a very excellent effect of controlling mites such as two-spotted spider mite, kanzawa spider mite, citrus red mite and the like.

The effect of the compounds according to the invention will be described with respect to the following test examples. Moreover, the following compounds are used as a comparative chemical, wherein a comparative chemical A is a compound described in Japanese Patent laid open No. 56-154464, and a comparative chemical B is a commercial product usually used for the control of mites.

Comparative chemical A 3,5-bis(o-chlorophenyl)-1-methyl-1H-1,2,4-triazole

Comparative chemical B

Hexythiazox (common name)

Test Example 1

Insecticidal test for diamond-back moth

The wettable powder prepared according to Formulation Example 2 is diluted with water so that the concentration of the active ingredient is 500 ppm. Cabbage leaves are immersed in the resulting diluted solution, dried in air and then placed in a vinyl chloride cup of 60 ml capacity. Ten larvae of 3rd instar diamond-back moth are released in the cup and thereafter a cover is placed thereon. Then, the cup is placed in a thermostatic chamber of 25° C. for 6 days, and the number of larvae died is counted to calculate the percentage of mortality. The test is carried out by double series. Moreover, the comparative chemical A is used for the comparison. The results are shown in Table 9.

TABLE 9

| Compound No. | Mortality (%) |
| --- | --- |
| 4 | 100 |
| 48 | 95 |
| 56 | 100 |
| 60 | 100 |
| 71 | 100 |
| 77 | 100 |
| 81 | 95 |
| 87 | 100 |
| 91 | 100 |
| 97 | 100 |
| 98 | 100 |
| 101 | 90 |
| 103 | 100 |
| 105 | 100 |
| 107 | 100 |
| 109 | 100 |
| 120 | 100 |
| 145 | 100 |
| 162 | 100 |
| 166 | 100 |
| 172 | 100 |
| 180 | 100 |
| 184 | 100 |
| 225 | 100 |
| Comparative chemical A | 20 |

Test Example 2

Insecticidal test for larvae of cotton aphid

The wettable powder prepared according to Formulation Example 2 is diluted with water so that the concentration of the active ingredient is 100 ppm. In the resulting diluted solution are immersed cucumber seedlings previously inoculated with larvae of cotton aphid and then subjected to a drying treatment in air. After the treatment, the cucumber seedlings are placed in a thermostatic chamber of 25° C. for 3 days and then the number of larvae died is counted to calculate the percentage of mortality. The test is carried out by double series. The results are shown in Table 10.

TABLE 10

| Compound No. | Mortality (%) |
| --- | --- |
| 2 | 100 |
| 4 | 100 |
| 11 | 100 |
| 12 | 100 |
| 24 | 100 |
| 27 | 100 |
| 28 | 100 |
| 29 | 100 |
| 45 | 100 |
| 46 | 100 |
| 47 | 100 |
| 52 | 100 |
| 67 | 100 |
| 71 | 100 |
| 80 | 100 |
| 81 | 100 |
| 87 | 100 |
| 92 | 100 |
| 93 | 100 |
| 95 | 100 |
| 97 | 100 |
| 99 | 100 |
| 105 | 100 |
| 107 | 100 |
| 109 | 100 |
| 120 | 100 |
| 143 | 100 |
| 145 | 100 |
| 162 | 100 |
| 166 | 100 |
| 172 | 100 |
| 176 | 100 |
| 180 | 100 |
| 184 | 100 |
| 225 | 100 |
| 226 | 100 |

Test Example 3

Ovicidal test for eggs of two-spotted spider mite

Female adults of two-spotted spider mite are placed on three leaf discs of kidney bean (diameter: 15 mm) and oviposited over 24 hours, and thereafter these adults are removed therefrom. The wettable powder prepared according to Formulation Example 2 is diluted with water so that the concentration of the active ingredient is 0.16 ppm. In the resulting diluted solution are immersed these leaf discs for 10 seconds. After the treatment, the leaf discs are placed in a thermostatic chamber of 25° C. for 7 days and then the number of unhatched eggs is counted to calculate the percentage of ovicidal activity. The test is carried out by double series. Moreover, the comparative chemicals A and B are used for the comparison. The results are shown in Table 11.

TABLE 11

| Compound No. | Mortality (%) |
| --- | --- |
| 47 | 100 |
| 97 | 100 |
| 98 | 100 |
| 143 | 100 |
| 162 | 100 |
| 166 | 100 |
| 172 | 100 |
| 184 | 100 |
| 225 | 100 |
| Comparative chemical A | 24 |
| Comparative chemical B | 95 |

Test Example 4

Ovicidal test for eggs of chemical-resistant kanzawa spider mite

Female adults of kanzawa spider mite having a resistance to commercially available chemicals are placed on three leaf discs of kidney bean (diameter: 15 mm) and oviposited over 2 days, and thereafter these adults are removed therefrom. The wettable powder prepared according to Formulation Example 2 is diluted with water so that the concentration of the active ingredient is 4 ppm. In the resulting diluted solution are immersed these leaf discs for 10 seconds. After the treatment, the leaf discs are placed in a thermostatic chamber of 25° C. for 7 days and then the number of unhatched eggs is counted to calculate the percentage of ovicidal activity. The test is carried out by double series. Moreover, the comparative chemicals A and B are used for the comparison. The results are shown in Table 12.

TABLE 12

| Compound No. | Mortality (%) |
| --- | --- |
| 2 | 100 |
| 3 | 100 |
| 4 | 100 |
| 5 | 100 |
| 6 | 100 |
| 10 | 100 |
| 11 | 100 |
| 14 | 100 |
| 21 | 100 |
| 22 | 100 |
| 24 | 100 |
| 27 | 100 |
| 28 | 100 |
| 29 | 100 |
| 31 | 100 |
| 38 | 100 |
| 42 | 100 |
| 43 | 100 |
| 45 | 100 |
| 46 | 100 |
| 48 | 100 |
| 50 | 100 |
| 52 | 100 |
| 54 | 100 |
| 56 | 100 |
| 58 | 100 |
| 60 | 100 |
| 64 | 100 |
| 66 | 100 |
| 71 | 100 |
| 75 | 100 |
| 77 | 100 |
| 78 | 100 |

TABLE 12-continued

| Compound No. | Mortality (%) |
|---|---|
| 80 | 100 |
| 81 | 100 |
| 87 | 100 |
| 91 | 100 |
| 93 | 100 |
| 95 | 100 |
| 97 | 100 |
| 98 | 100 |
| 99 | 100 |
| 101 | 100 |
| 103 | 100 |
| 107 | 100 |
| 109 | 100 |
| 172 | 100 |
| 184 | 100 |
| Comparative chemical A | 31 |
| Comparative chemical B | 0 |

Test Example 5

Insecticidal test for larvae of chemical-resistant kanzawa spider mite

Female adults of kanzawa spider mite having a resistance to commercially available chemicals are placed on three leaf discs of kidney bean (diameter: 15 mm) and oviposited over 2 days, and thereafter these adults are removed therefrom. Then, these leaf discs are placed in a thermostatic chamber of 25° C. for 5 days and the number of hatched larvae is counted. Separately, the wettable powder prepared according to Formulation Example 2 is diluted with water so that the concentration of the active ingredient is 20 ppm. After these leaf discs are sprayed with the resulting diluted solution, they are placed in a thermostatic chamber of 25° C. for 7 days and then the number of living adults is counted to calculate the percentage of mortality on the hatched larvae. The test is carried out by double series. Moreover, the comparative chemicals A and B are used for the comparison. The results are shown in Table 13.

TABLE 13

| Compound No. | Mortality (%) |
|---|---|
| 97 | 100 |
| 98 | 100 |
| 172 | 100 |
| 184 | 100 |
| Comparative chemical A | 55 |
| Comparative chemical B | 25 |

Test Example 6

Ovicidal test for eggs of citrus red mite

Female adults of citrus red mite are placed on two laminate of citrus fruit (diameter: 10 mm) and oviposited over 2 days, and thereafter these adults are removed therefrom. The wettable powder prepared according to Formulation Example 2 is diluted with water so that the concentration of the active ingredient is 4 ppm. In the resulting diluted solution are immersed these laminate for 10 seconds. After the treatment, the laminate are placed in a thermostatic chamber of 25° C. for 7 days and then the number of unhatched eggs is counted to calculate the percentage of ovicidal activity. The test is carried out by double series. Moreover, the comparative chemicals A and B are used for the comparison. The results are shown in Table 14.

TABLE 14

| Compound No. | Mortality (%) |
|---|---|
| 97 | 100 |
| Comparative chemical A | 33 |
| Comparative chemical B | 90 |

What is claimed is:

1. A triazole derivative having the following general formula [I]:

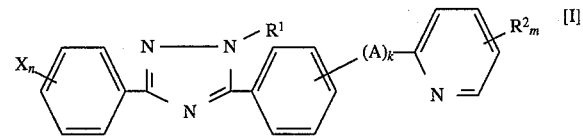

(wherein $R^1$ is an alkyl ($C_1$–$C_6$) group, X is a hydrogen atom, a halogen atom, an alkyl ($C_1$–$C_6$) group, an alkoxy ($C_1$–$C_6$) group, an alkylthio ($C_1$–$C_6$) group, a nitro group, a cyano group or trifluoromethyl group, n is an integer of 1–5 provided that when n is 2 or more, X may be an optional combination of same or different atoms or groups, A is an oxygen atom, a sulfur atom, an alkylene ($C_1$–$C_4$) group, an alkyleneoxy ($C_1$–$C_4$) group, an oxyalkylene ($C_1$–$C_4$) group or an alkyleneoxy($C_1$–$C_4$)alkylene ($C_1$–$C_4$) group, k is 0 or 1, $R^2$ is a hydrogen atom, a halogen atom, an alkyl ($C_1$–$C_6$) group, an alkoxy ($C_1$–$C_6$) group, trifluoromethyl group or trifluoromethoxy group, and m is an integer of 1–5 provided that when m is 2 or more, $R^2$ may be an optional combination of same or different atoms or groups).

2. A triazole derivative according to claim 1, wherein said $R^1$ is a straight or branched-chain alkyl ($C_1$–$C_6$) group, X is a hydrogen atom, a halogen atom, a straight or branched-chain alkyl ($C_1$–$C_4$) group, a nitro group, a cyano group or trifluoromethyl group, n is an integer of 1–3 provided that when n is 2 or 3, X may be an optional combination of same or different atoms or groups, A is an oxygen atom, a sulfur atom, an alkylene ($C_1$–$C_2$) group, an alkyleneoxy ($C_1$–$C_2$) group, an oxyalkylene ($C_1$–$C_2$) group or an alkyleneoxy($C_1$–$C_2$)alkylene ($C_1$–$C_2$) group, k is 0 or 1, $R^2$ is a hydrogen atom, a halogen atom, an alkyl ($C_1$–$C_6$) group or trifluoromethyl group, and m is an integer of 1–3 provided that when m is 2 or 3, $R^2$ may be an optional combination of same or different atoms or groups.

3. A triazole derivative according to claim 1, wherein said $R^1$ is methyl group, X is a halogen atom, n is 1 or 2 provided that when n is 2, X may be an optional combination of same or different atoms, A is an oxygen atom or an alkyleneoxy ($C_1$–$C_2$) group, k is 0 or 1, $R^2$ is a hydrogen atom, a halogen atom, an alkyl ($C_1$–$C_3$) group or trifluoromethyl group, and m is an integer of 1–3 provided that when m is 2 or 3, $R^2$ may be an optional combination of same or different atoms or groups.

4. An insecticidal and acaricidal composition comprising an insecticidally and acaricidally effective amount of triazole derivative as defined in claim 1 and a carrier.

5. An insecticidal and acaricidal composition comprising an insecticidally and acaricidally effective amount of triazole derivative as defined in claim 2 and a carrier.

6. An insecticidal and acaricidal composition comprising an insecticidally and acaricidally effective amount of triazole derivative as defined in claim 3 and a carrier.

7. A method of killing insects, aphids or mites or their eggs or larvae, comprising applying to a site infested or liable to infestation therewith an insecticidally and acaricidally effective amount of triazole derivative having the following general formula (I):

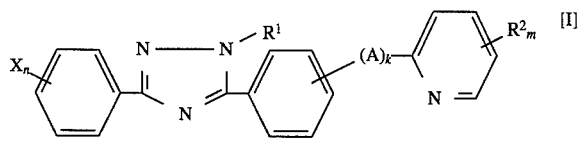

(wherein $R^1$ is an alkyl ($C_1$–$C_6$) group, X is a hydrogen atom, a halogen atom, an alkyl ($C_1$–$C_6$) group, an alkoxy ($C_1$–$C_6$) group, an alkylthio ($C_1$–$C_6$) group, a nitro group, a cyano group or trifluoromethyl group, n is an integer of 1–5 provided that when n is 2 or more, X may be an optional combination of same or different atoms or groups, A is an oxygen atom, a sulfur atom, an alkylene ($C_1$–$C_4$) group, an alkyleneoxy ($C_1$–$C_4$) group, an oxyalkylene ($C_1$–$C_4$) group or an alkyleneoxy($C_1$–$C_4$)alkylene ($C_1$–$C_4$) group, k is 0 or 1, $R^2$ is a hydrogen atom, a halogen atom, an alkyl ($C_1$–$C_6$) group, an alkoxy ($C_1$–$C_6$) group, trifluoromethyl group or trifluoromethoxy group, and m is an integer of 1–5 provided that when m is 2 or more, $R^2$ may be an optional combination of same or different atoms or groups).

8. A method of killing insects, aphids or mites or their eggs or larvae, comprising applying to a site infested or liable to infestation therewith an insecticidally and acaricidally effective amount of triazole derivative having the following general formula (I):

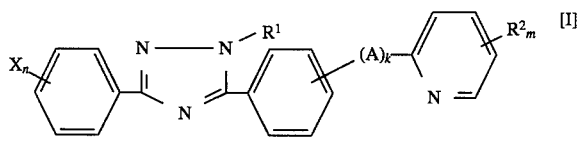

(wherein said $R^1$ is a straight or branched-chain alkyl ($C_1$–$C_6$) group, X is a hydrogen atom, a halogen atom, a straight or branched-chain alkyl ($C_1$–$C_4$) group, a nitro group, a cyano group or trifluoromethyl group, n is an integer of 1–3 provided that when n is 2 or 3, X may be an optional combination of same or different atoms or groups, A is an oxygen atom, a sulfur atom, an alkylene ($C_1$–$C_2$) group, an alkyleneoxy ($C_1$–$C_2$) group, an oxyalkylene ($C_1$–$C_2$) group or an alkyleneoxy($C_1$–$C_2$)alkylene ($C_1$–$C_2$) group, k is 0 or 1, $R^2$ is a hydrogen atom, a halogen atom, an alkyl ($C_1$–$C_6$) group or trifluoromethyl group, and m is an integer of 1–3 provided that when m is 2 or 3, $R^2$ may be an optional combination of same or different atoms or groups).

9. A method of killing insects, aphids or mites or their eggs or larvae, comprising applying to a site infested or liable to infestation therewith an insecticidally and acaricidally effective amount of triazole derivative having the following general formula (I):

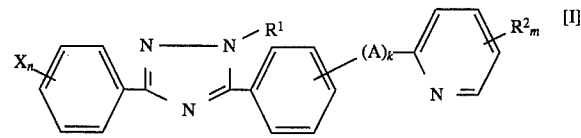

(wherein said $R^1$ is methyl group, X is a halogen atom, n is 1 or 2 provided that when n is 2, X may be an optional combination of same or different atoms, A is an oxygen atom or an alkyleneoxy ($C_1$–$C_2$) group, k is 0 or 1, $R^2$ is a hydrogen atom, a halogen atom, an alkyl ($C_1$–$C_3$) group or trifluoromethyl group, and m is an integer of 1–3 provided that when m is 2 or 3, $R^2$ may be an optional combination of same or different atoms or groups).

* * * * *